United States Patent [19]
Udagawa et al.

[11] Patent Number: 5,243,612
[45] Date of Patent: Sep. 7, 1993

[54] CANCER THERAPY SYSTEM

[75] Inventors: Takeshi Udagawa, Kawasaki; Takeyasu Amano, Yokohama; Hiroyuki Shiozaki, Yokosuka; Mikio Mori, Musashino; Sadao Degawa, Komae; Harubumi Kato, Tokyo, all of Japan

[73] Assignee: Ishikawajima-Harima Jukogyo Kabushiki Kaisha, Tokyo, Japan

[21] Appl. No.: 924,479

[22] Filed: Aug. 4, 1992

[30] Foreign Application Priority Data

Aug. 5, 1991 [JP] Japan .................. 3-219189

[51] Int. Cl.⁵ ............................. H01S 3/10
[52] U.S. Cl. ............................. 372/22
[58] Field of Search ............... 372/22, 23; 385/116, 385/117; 359/328, 330; 606/5, 7, 10; 128/6

[56] References Cited

U.S. PATENT DOCUMENTS 4,866,720  9/1989  Holly ........................ 372/22
4,887,270 12/1989  Austin ....................... 372/22

FOREIGN PATENT DOCUMENTS

0429297A2  5/1991  European Pat. Off. .
58-64307   4/1983  Japan .
62-11440   1/1987  Japan .
63-2633    1/1988  Japan .
63-23648   1/1988  Japan .
63-9464    2/1988  Japan .
2126717A   3/1984  United Kingdom .

OTHER PUBLICATIONS

Leo's 90 IEEE Lasers and Electro-Optics Society Annual Meeting, Conference Proceedings. vol. 2, Nov. 4, 1990, New York, U.S. pp. 524–525, H. H. Zenzie et al. "Harmonic Generation of TI:Sapphire Lasers" p. 524.
Patent Abstracts of Japan, vol. 15, No. 184 P(-1200) May 13, 1991 and JP-A-03 042 550, (Tosoh) Feb. 22, 1991 *Abstract*.

*Primary Examiner*—John D. Lee
*Assistant Examiner*—Robert E. Wise
*Attorney, Agent, or Firm*—Oblon, Spivak, McClelland, Maier & Neustadt

[57] ABSTRACT

In a solid-state laser, a YAG laser generates laser beam with a predetermined wavelength in response to which a titanium-sapphire laser is pumped to generate laser beam with a predetermined wavelength which is administered through a fiberscope to irradiate focuses, treating or destroying the same.

6 Claims, 6 Drawing Sheets

CANCER THERAPY SYSTEM

BACKGROUND OF THE INVENTION

The present invention relates to a cancer therapy system.

Japanese Patent 2nd Publication No. 63-2633 discloses a cancer therapy system using laser beam pulse in which laser beam with a predetermined wavelength is irradiated on cancerous focuses to which photosensitive substance having affinity with cancer tissues has been absorbed, thereby destroying the focuses.

Japanese Patent 2nd Publication No. 63-9464 discloses a cancer diagnosis system using laser beam pulse in which laser beam with a predetermined wavelength is irradiated on focuses to which photosensitive substance having affinity with cancer tissues has been absorbed and fluorescence from the substance absorbed in the focuses is subjected to fluorescence analysis to thereby diagnose whether a cancer has grown on the target area.

In these conventional systems, an excimer laser is used to pump a dye laser so as to produce laser beam with a predetermined wavelength.

Laser medium used in dye lasers, which is a liquid such as alcohol or solvent having an organic pigment dye dissolved therein, has a short service life so that pigment dye has to be frequently exchanged. Moreover, mirror means in excimer lasers has to be frequently cleaned.

The present invention was made to overcome the above and other problems encountered in the prior art and has for its object to provide a cancer therapy system which utilizes solid-state laser and is easy in operation and maintenance.

BRIEF SUMMARY OF THE INVENTION

The present invention provides a cancer therapy system comprising a solid-state laser unit having a YAG laser oscillator for producing YAG laser fundamental wave, a YAG laser second harmonic generator for producing YAG laser second harmonic from the fundamental wave produced by said YAG laser oscillator, a titanium-sapphire laser which is pumped by the YAG laser second harmonic generated by said YAG laser second harmonic generator to generate titanium-sapphire laser fundamental wave, a titanium-sapphire laser second harmonic generator for generating titanium-sapphire laser second harmonic from said titanium-sapphire laser fundamental wave generated by said titanium-sapphire laser, a difference-frequency-generating YAG laser second harmonic generator which generates YAG laser second harmonic from the YAG laser fundamental wave having not converted to said YAG laser second harmonic by said second harmonic generator, a difference-frequency-generating titanium-sapphire laser oscillator which is pumped by the YAG laser second harmonic generated by said second harmonic generator to generate titanium-sapphire laser beam fundamental wave and a difference frequency generator which generates difference frequency laser beam from the titanium-sapphire laser fundamental wave generated by said difference-frequency-generating titanium-sapphire laser oscillator and the titanium-sapphire laser second harmonic generated by said titanium-sapphire laser second harmonic generator, a fiberscope for irradiating focuses with the laser beam generated by said solid-state laser unit and for observation of said focuses, and an image display unit for photographing said focuses through said fiberscope and displaying an image of said focuses.

In another aspect of the invention, a cancer therapy system comprises a solid-state laser unit having a YAG laser oscillator for producing YAG laser fundamental wave, a YAG laser second harmonic generator for producing YAG laser second harmonic from the fundamental wave produced by said YAG laser oscillator, a titanium-sapphire laser oscillator which is pumped by said YAG laser second harmonic generated by said YAG laser second harmonic generator to generate titanium-sapphire laser fundamental wave, a titanium-sapphire laser second harmonic generator for generating titanium-sapphire laser second harmonic from said titanium-sapphire laser fundamental wave generated by said titanium-sapphire laser oscillator, a YAG laser third harmonic generator for generating the YAG laser third harmonic from the YAG laser fundamental wave having not been converted to the second harmonic by said YAG laser second harmonic generator and the YAG second harmonic generated by said YAG laser second harmonic generator and an optical parametric oscillator for generating optical parametric oscillating laser beam from the YAG laser third harmonic generated by said YAG laser third harmonic generator, fiberscope for irradiating focuses with the laser beam generated by said solid-state laser unit and observing said focuses and an image display unit for viewing said focuses through said fiberscope and displaying an image of said focuses.

In any of the system, the image display unit capable of viewing said focuses through the fiberscope may serve to graphically display a spectrum of florescence from said focuses or fluorescent positions on said focuses.

With any of the system, laser beam to be guided to the focuses is produced by the solid-state laser unit so that the operating lifetime can be increased and maintenance operation is much facilitated.

DETAILED DESCRIPTION OF THE PREFERRED EMBODIMENTS

Now the present invention will become more apparent from the following description of preferred embodiments thereof taken in conjunction with the accompanying drawings.

Figure 1:
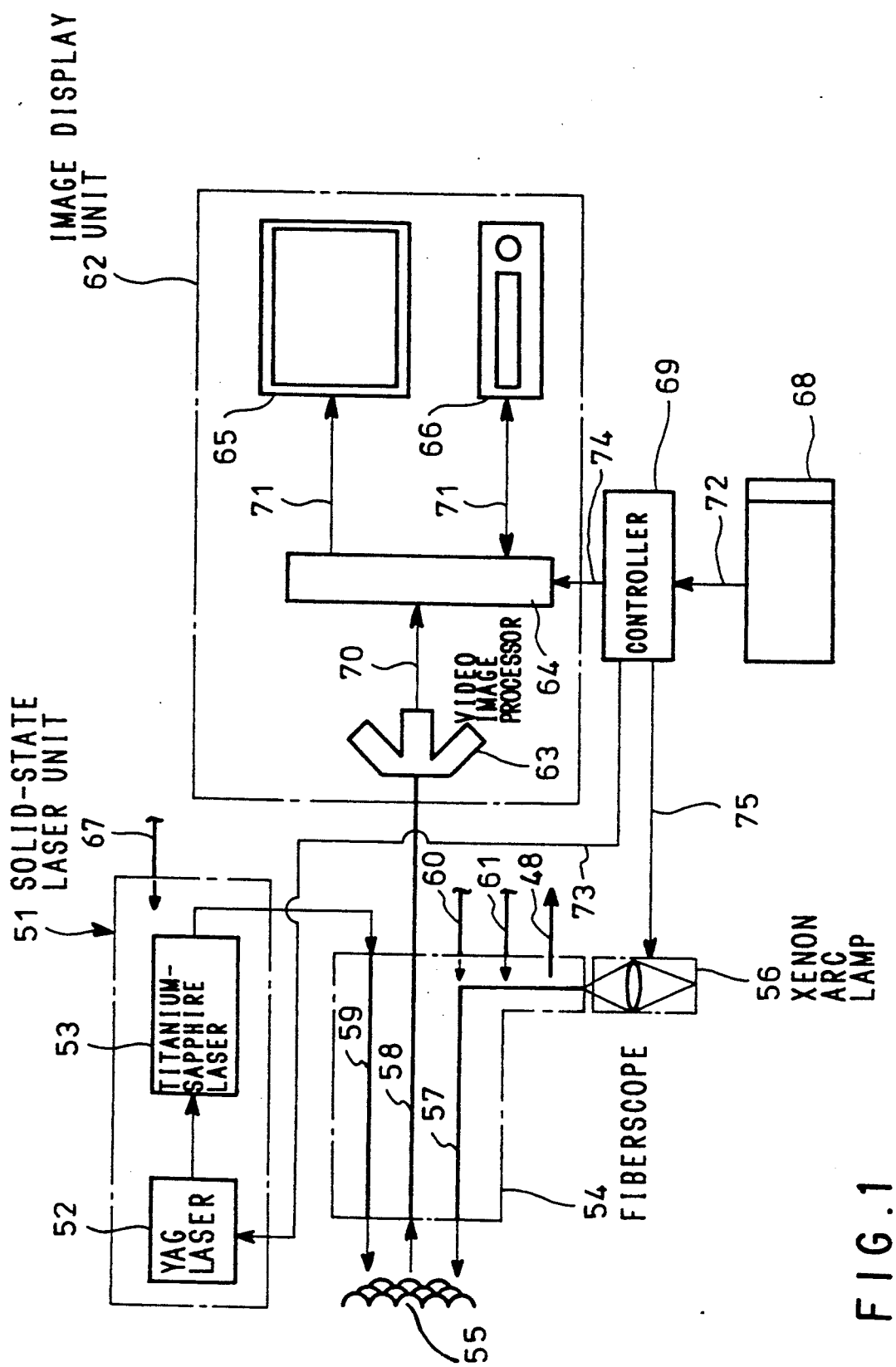
FIG. 1 is a schematic diagram of a first embodiment of the present invention.
Figure 2:
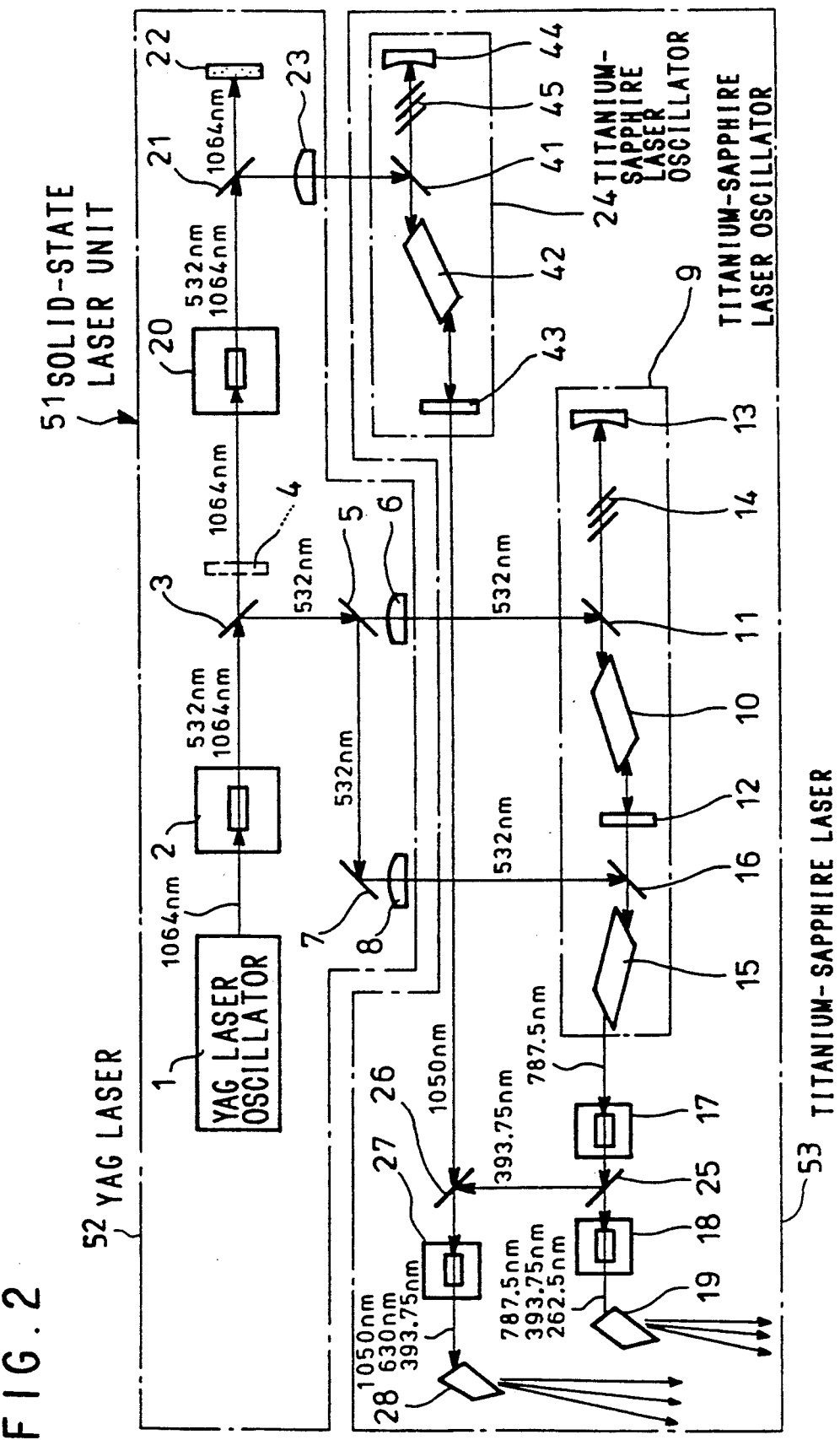
FIG. 2 is a schematic diagram of a solid-state laser unit shown in FIG. 1.

FIGS. 1 and 2 show a first embodiment of a cancer therapy system according to the present invention which corresponds to Claim 1 to be defined hereinafter.

A solid-state laser unit generally indicated by numeral 51 comprises a YAG laser 52 which emits laser beam with a predetermined wavelength and a titanium-sapphire laser 53 which is pumped by the laser beam from the YAG laser 52 to emit laser beam with a predetermined wavelength.

The laser unit 51 is connected with a supply pipe 67 through which cooling water is supplied to the laser 52 so as to prevent overheating of the latter.

A fiberscope generally designated by numeral 54 serves for observation and treatment of focuses 55 and comprises illuminating optical fiber 57 which is optically connected to a high-intensity illuminating source such as a xenon arc lamp 56 to illuminate the focuses 55 and picturing or imaging optical fiber 58 through which an operator, physician or the like observes the focuses 55 and irradiating optical fiber 59 through which laser beam from the laser unit 51 is transmitted to the focuses 55.

The fiberscope 54 is coupled with supply pipes 60 and 61 through which cleaning water and air are respectively sent to and clean tip ends of the fibers 57, 58 and 59 and is coupled with a discharge pipe 48 for discharging waste water and air.

An image display unit generally indicated by numeral 62 serves to observe or diagnose the focuses 55 and comprises a color television camera 63 for viewing the focuses 55 through the fiber 58 and delivering a video signal 70, a video image processor 64 for converting the signal 70 from the camera 63 into a processed video signal 71, a monitor television 65 which receives the signal 71 from the processor 64 to display the image of the focuses 55 and a video recording/reproducing device 66 such as a video tape recorder 66 which receives and records the signal 71 from the processor 64 and transmits the recorded signal 71 to the processor 64 so that the recorded image of the focuses 55 may be displayed on the television 65 when so required.

The first embodiment further includes a control panel 68 which is manually operated by an operator to control the solid-state laser unit 51, the image display unit 62 and the xenon arc lamp 56 by sending control signals 72. In response to the signals 72 from the panel 68, a controller 69 delivers control signals 73, 74 and 75 to the laser 52, the processor 64 and the lamp 56, respectively, thereby activating or deactivating the units 51, 62 and the lamp 56, respectively.

Referring next to FIG. 2, the YAG laser 52 in the solid-state laser unit 51 will be described in detail.

Reference numeral 1 designates a YAG laser oscillator which generates laser beam or YAG laser fundamental wave with a wavelength of 1064 nm to be used for pumping; 2, a YAG laser second harmonic generator which, in response to the laser fundamental wave from the oscillator 1, generates laser beam with a wavelength of 532 nm or YAG laser second harmonic under the condition $$\frac{1}{\lambda_2} = \frac{1}{\lambda_1} + \frac{1}{\lambda_1} \quad (1)$$

where $\lambda_1$ is wavelength of fundamental wave and $\lambda_2$ is wavelength of second harmonic; 3, a dichroic mirror which permits, among the YAG laser fundamental wave from the oscillator 1 remaining without being converted into the second harmonic and the YAG laser second harmonic from the generator 2, transmission of only the fundamental wave and reflects the second harmonic; and 4, a beam damper which cuts off the YAG laser fundamental wave having passed through the mirror 3; 5, a half-mirror which transmits part of the second harmonic reflected from the mirror 3 and reflects the remaining second harmonic; 6, a lens for converging the second harmonic which has transmitted through the half-mirror 5; 7, a total reflection mirror for reflecting the second harmonic reflected from the half-mirror 5; and 8, a lens for converging the second harmonic reflected from the mirror 7.

Reference numeral 20 designates a second harmonic generator which, as in the case of the generator 2, generates laser beam with the wavelength of 532 nm (or YAG laser second harmonic) from the YAG laser fundamental wave with the wavelength of 1064 nm which has passed through the mirror 3, in accordance with the relation (1) described above; 21 a dichroic mirror which, among the YAG laser fundamental wave which has not converted into the second harmonic by the generator 20 and the second harmonic generated by the generator 20, transmits only the YAG laser fundamental wave and reflects the second harmonic; 22, a beam damper for cutting off the YAG laser fundamental wave having passed through the mirror 21; and 23, a lens for converging the YAG laser second harmonic reflected from the mirror 21.

It is to be noted here that with the YAG laser 52 with the above-described construction, the beam damper 4 capable of cutting off the fundamental wave with the wavelength of 1064 nm may be interposed between the mirror 3 and the generator 20.

Next referring still to FIG. 2, the titanium-sapphire laser 53 in the solid-state laser unit 51 will be described in more detail.

Reference numeral 9 denotes a titanium-sapphire laser oscillator which comprises a dichroic mirror 11 for reflecting the YAG laser second harmonic having been converged by the lens 6 and transmits beams with other wavelengths; a titanium-sapphire laser rod 10 which is pumped in response to incidence of the YAG laser second harmonic reflected from the mirror 11 to generate beam with the wavelength of 670 to 1100 nm; front and end mirrors 12 and 13 of a resonator for causing the resonance of beam from the rod 10; a wavelength tuning or selection element 14 such as a double refraction filter which, among beam with the wavelength ranging from 670 to 1100 nm emitted from the rod 10, transmits beam with a predetermined wavelength and absorbs beams with other wavelengths; a dichroic mirror 16 which transmits the titanium-sapphire laser fundamental wave with a wavelength between 670 and 1100 nm and having reached a predetermined intensity during the resonance between the mirrors 12 and 13 and reflects the YAG laser second harmonic converged by the lens 8; and a titanium-sapphire laser amplification rod 15 which is pumped in response to the incidence of the YAG laser second harmonic reflected from the mirror 16 to amplify the intensity of the incident titanium-sapphire fundamental wave after having passed through the mirror 16.

With the laser oscillator 9 of the type described above, the wavelength of the titanium-sapphire laser fundamental wave from the oscillator 9 can be arbitrarily selected within the wavelength range between 670 and 1100 nm by angularly displacing the element 14.

Reference numeral 17 designates a second harmonic generator for generating titanium-sapphire laser second harmonic from the titanium-sapphire fundamental wave emitted from the rod 15 in the oscillator 9 in accordance with the relation (1) described above; and 18, a titanium-sapphire laser third harmonic and fourth harmonic generator which generates titanium-sapphire laser third harmonic from the titanium-sapphire laser second harmonic generated by the generator 17 and the titanium-sapphire laser fundamental wave having not been converted into the second harmonic in accordance with the following relation $$\frac{1}{\lambda_3} = \frac{1}{\lambda_1} + \frac{1}{\lambda_2} \quad (2)$$

where $\lambda_1$: wavelength of fundamental wave,
$\lambda_2$: wavelength of second harmonic and
$\lambda_3$: wavelength of third harmonic
or generates a titanium-sapphire laser fourth harmonic (second harmonic of second harmonic) from the titanium-sapphire laser second harmonic in accordance with the relation (1) described above.

The generator 18 is adapted to receive therein a crystal cell containing a non-linear optical crystal capable of generating the third harmonic or a crystal cell containing a non-linear optical crystal capable of generating the fourth harmonic. It follows therefore that exchange of such crystal cells enables alternative generation of titanium-sapphire laser third or fourth harmonic.

Reference numeral 19 denotes a pellinbroca prism for separating the titanium-sapphire laser fundamental wave and second harmonic which have not been converted by the generator 18 and the titanium-sapphire laser third or fourth harmonic generated by the generator 18.

A difference-frequency-generating titanium-sapphire laser oscillator generally designated by numeral 24 generates difference frequency and comprises a dichroic mirror 41 which reflects the YAG laser second harmonic converged by the lens 23 and passes beams with other wavelengths; a titanium-sapphire laser rod 42 which is pumped in response to incidence of the YAG laser second harmonic reflected from the mirror 41 to generate beam with the wavelength between 670 and 1100 nm; front and end mirrors 43 and 44 for causing resonance of beam emitted from the rod 42; and a wavelength tuning or selection element 45 such as a double refraction filter which passes beam only with a predetermined wavelength among beam with wavelength ranging between 670 and 1100 nm emitted from the rod 42 and scatters beams with other wavelengths.

With the oscillator 24 of the type described above, the wavelength of the fundamental wave emitted from the oscillator 24 can be arbitrarily selected within the wavelength range between 670 and 1100 nm by angularly displacing the element 45.

A dichroic mirror 25 is removably interposed between the generators 17 and 18 and passes only the titanium-sapphire laser fundamental wave which has not been converted to the second harmonic by the generator 17 and reflects the titanium-sapphire laser second harmonic generated by the generator 17. A dichroic mirror 26 reflects the second harmonic from the mirror 25 and passes only the titanium sapphire laser fundamental wave from the oscillator 24. A difference frequency generator 27 produces difference frequency laser beam from the titanium-sapphire laser second harmonic reflected from the mirror 26 and the titanium-sapphire laser fundamental wave transmitted through the mirror 26 in accordance with the following relation of differential frequency wave being generated $$\frac{1}{\lambda_6} = \frac{1}{\lambda_5} - \frac{1}{\lambda_4} \quad (3)$$

where
$\lambda_6$: wavelength of differential frequency wave,
$\lambda_4$: wavelength of beam wave A,
$\lambda_5$: wavelength of beam wave B and
$\lambda_4 > \lambda_5$.

A pellinbroca prism 28 separates the titanium-sapphire laser second harmonic (beam wave B) remaining downstream of the generator 27, the titanium-sapphire laser fundamental wave (beam wave A) also remaining downstream of the generator 27 and the difference frequency laser beam emitted from the generator 27.

Next, mode of operation of the first embodiment will be described.

Upon therapy of the focuses 55, optical characteristics of the wavelength tuning element 14 in the oscillator 9 are so adjusted that laser beam with the wavelength of 787.5 nm is permitted to pass and laser beam with other wavelengths is absorbed. Optical characteristics of the wavelength tuning element 45 in the difference-frequency-generating titanium-sapphire laser 24 are also so adjusted that the laser beam with the wavelength of 1050 nm is permitted to pass through and absorbs laser beams with other wavelengths. Then, the dichroic mirror 25 is interposed between the generators 17 and 18.

Moreover, a hematoporphyrin derivative (hereinafter referred to as HPD), which has affinity with cancerous tissues and is a photosensitive substance, is injected into a blood vessel of a patient so that HPD is preliminarily absorbed by the focuses 55.

HPD is specifically absorbed by cancerous tissues and is hardly absorbed by normal tissue.

When being irradiated with the laser beam with the wavelength of 630 nm, the HPD-laden cancerous focuses 55 are destroyed; whereas normal tissues with HPD being hardly absorbed are not adversely affected at all by irradiation of the same laser beam.

After the focuses 55 has absorbed HPD, the fiberscope 54 is positioned such that its tip end is substantially in opposing relationship with the focuses 55.

Under this condition, the control panel 68 is manually operated to transmit the command signal 72 to the controller 69 so as to activate the image display unit 62 as well as the arc lamp 56, so that the controller 69 transmits the command signals 74 and 75 to the video image processor 64 and the lamp 56, respectively, thereby activating them. Then, the beam from the lamp 56 illuminates the focuses 55. Image of the focuses 55 picked up by the color television camera 63 is displayed on the monitor television 65, whereby the focuses 55 are observed and diagnosed.

Thereafter, the control panel 68 is manually operated again to transmit the command signal 72 to the controller 69 which transmits the command signal 73 to the YAG laser 52 in the solid-state laser unit 51 to energize the same. In response to the command signal 73 applied to the YAG laser 52, the YAG laser oscillator 1 is energized so that the laser beam with the wavelength of 1064 nm (the YAG laser fundamental weave) is produced. In response to the laser beam thus produced, the generator 2 generates the YAG laser second harmonic with the wavelength of 532 nm which is then reflected by the mirror 3. Part of the YAG laser second harmonic reflected from the mirror 3 passes through the half-mirror 5, the lens 6 and the mirror 11 and enters the laser rod 10 of the oscillator 9 so that the titanium-sapphire laser fundamental wave with a wavelength between 670 and 1100 nm is oscillated.

The fundamental wave again enters the rod 10 by means of the mirrors 12 and 13. Thereafter, only the fundamental wave with the wavelength of 787.5 nm passes through the wavelength tuning element 14 while the fundamental waves with other wavelengths are absorbed by the element 14. When the intensity of the titanium-sapphire laser fundamental wave with the wavelength of 787.5 nm reaches a predetermined level, the titanium-sapphire fundamental wave passes through the mirrors 12 and 16 and enters the laser amplification rod 15.

Meanwhile, part of the YAG laser second harmonic from the mirror 3 is reflected by the half-mirror 5 toward the total reflection mirror 7 which in turn reflects the second harmonic to the lens 8. The YAG laser second harmonic having passed through the lens 8 enters, as the pumping beam, the laser amplification rod 15 in the oscillator 9 so that the rod 15 is pumped and the titanium-sapphire laser fundamental wave with the wavelength of 787.5 nm emitted from the laser rod 10 and entering the amplification rod 15 is amplified.

The titanium-sapphire laser fundamental wave with the wavelength of 787.5 nm and amplified by the rod 15 enters the titanium-sapphire laser second harmonic generator 17 which generates the titanium-sapphire laser second harmonic with the wavelength of 393.75 nm in accordance with the relation (1) described above. The titanium-sapphire laser second harmonic generated by the generator 17 upon transmission of the titanium-sapphire laser fundamental wave to the generator 17 is reflected by the mirror 25 whereas the titanium-sapphire laser fundamental wave having passed through the generator 17 is transmitted through the dichroic mirror 25.

The second harmonic reflected from the mirror 25 is reflected by the mirror 26 to be redirected to the difference frequency generator 27.

Meanwhile, the YAG laser fundamental wave which is transmitted through the mirror 3 enters the difference-frequency-generating YAG laser second harmonic generator 20 which generates the YAG laser second harmonic with the wavelength of 532 nm in accordance with the relation (1) described above. The YAG laser second harmonic thus generated is directed as the pumping beam by the optical elements such as the dichroic mirror 21 and the lens 23 to the difference-frequency-generating titanium-sapphire laser oscillator 24 which generates the titanium-sapphire laser fundamental wave with the wavelength of 1050 nm which in turn is transmitted through the dichroic mirror 26 to the difference frequency generator 27.

In response to the incidence of the titanium-sapphire laser fundamental wave with the wavelength of 1050 nm and the titanium-sapphire laser second harmonic with the wavelength of 393.75 nm, the difference frequency generator 27 generates the laser beam with the wavelength of 630 nm from the titanium-sapphire laser fundamental wave and second harmonic in accordance with the relation (3) described above. The titanium-sapphire laser fundamental wave and second harmonic transmitted through the generator 27 and the laser beam with the wavelength of 630 nm generated by the generator 27 are separated from each other by the prism 28.

The laser beam with the wavelength of 630 nm separated by the prism 28 is transmitted through the irradiating optical fiber 59 in the fiberscope 54 and is irradiated to the focuses 55, whereby the cancerous tissues with HPD being absorbed are destroyed by the laser beam with the wavelength of 630 nm.

So far the first embodiment has been described with reference to the case where HPD is used. When other photo-sensitive substance is used, the optical characteristics of the wavelength tuning elements 14 and 45 are varied to match the wavelengths of the laser beams generated by the titanium-sapphire laser second harmonic generator 17 and the difference frequency generator 27 with characteristic or absorption band of the photosensitive substance to be used.

Figure 3:
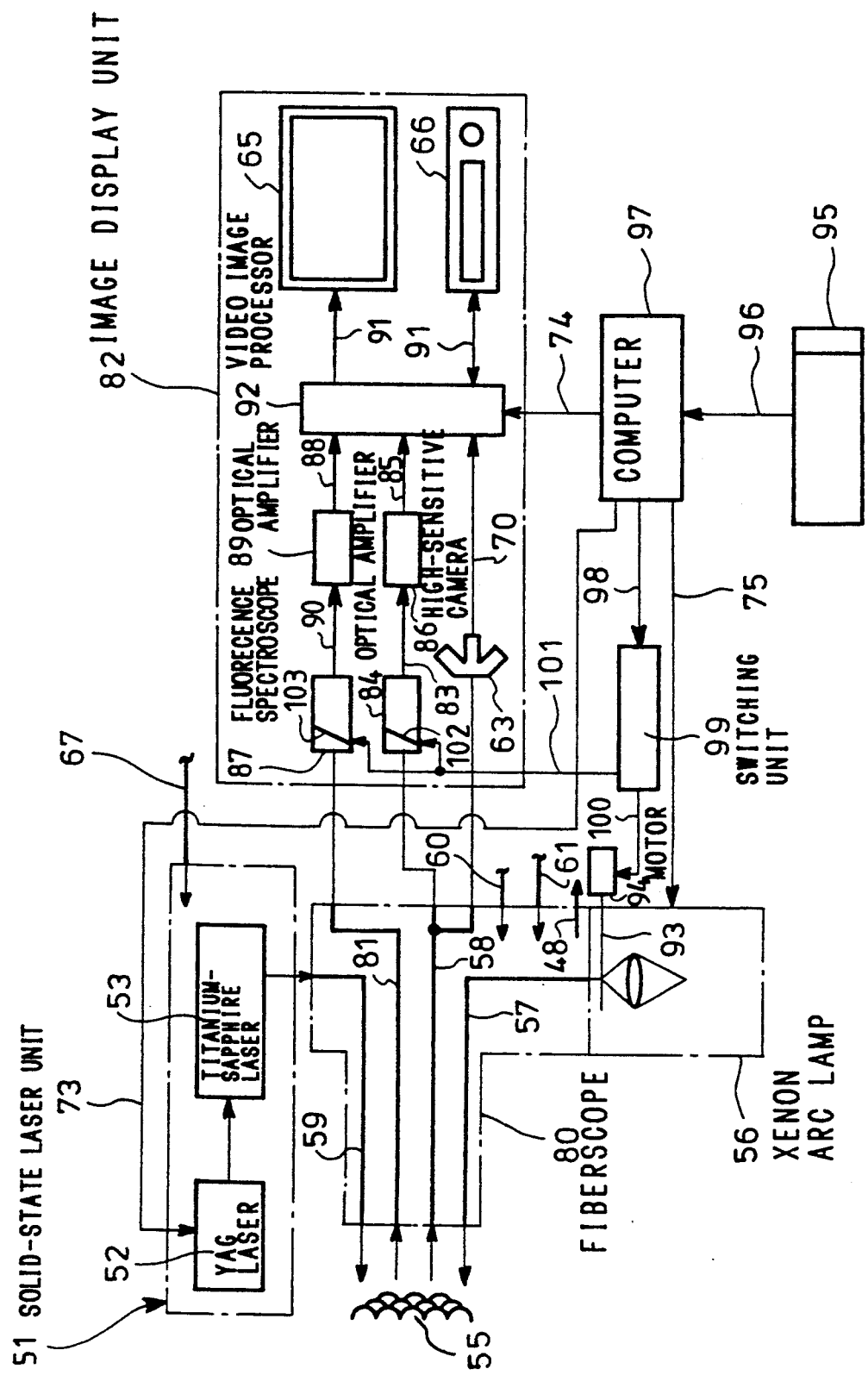
FIG. 3 is a schematic diagram of a second embodiment of the present invention.

FIG. 3 is a schematic diagram of a second embodiment of the present invention which corresponds to Claims 2 and 3 mentioned hereinafter. The solid-state laser unit 51 shown in FIG. 3 is substantially similar in construction to that described above with reference to FIGS. 1 and 2 and the parts similar to those shown in FIGS. 1 and 2 are designated by the reference numerals same as shown in FIGS. 1 and 2.

Reference numeral 80 denotes a fiberscope for observing, diagnosing and treating the focuses 55 which is substantially similar in construction to the fiberscope 54 shown in FIG. 1 except that the fiberscope 80 further incorporates a diagonosing optical fiber 81.

The xenon arc lamp 56 which generates illumination light to be transmitted through the fiberscope 80 incorporates an optical chopper 93 so that beam for illuminating the focuses 55 can be transmitted intermittently.

The optical chopper 93 has a disk which is formed with a plurality of holes arranged in a desired pattern and is rotated by a motor 94 so that light from the lamp 56 can be intermittently transmitted to the focuses 55.

An image display unit generally designated by numeral 82 for observing and diagnosing the focuses 55 comprises a color television camera 63 for picking up the image of the focuses 55 through an imaging fiber 58 and outputting a video signal 70; an optical amplifier 84 for receiving fluorescence from the focuses 55 through the fiber 58. amplifying the received fluorescence and delivering an amplified fluorescence signal 83; a high-sensitive camera 86 for converting the signal 83 from the amplifier 84 into a video signal 85; a fluorescence spectroscope 87 for receiving the fluorescence from the focuses 55 through the diagnosing optical fiber 81 and resolving a fluorescent radiation with a predetermined wavelength; an optical amplifier 89 for receiving a fluorescent radiation 90 from the spectroscope 87, amplifying it and delivering a video signal 88; a video image processor 92 for receiving the signals 70, 85 and 88 respectively from the cameras 63 and 86 and amplifier 89 and converting them into a processed video signal 91; a monitor television 65 for displaying the image of the focuses 55, the image of fluorescent positions on the focuses 55 or a fluorescent spectrum from the focuses 55; and a recording/reproducing unit 66 for recording the processed video signal 91 from the processor 92 and transmitting the recorded signal 91 to the monitor television 65 through the processor 92, thereby displaying the image of the focuses 55, the image of the fluorescent positions on the focuses 55 or the fluorescent spectrum from the focuses 55.

Furthermore, as shown in FIG. 3, the second embodiment further includes a control panel 95 which is manually operated to transmit a command signal 96 for activating the solid-state laser unit 51, the video image display unit 82, the xenon arc lamp 56 and the optical chopper 93, depending upon observation, diagnosis and treatment to be carried out; and a computer 97 which, in response to the command signal 96, delivers an actuating signal 73 to the YAG laser 52 so as to energize the solid-state laser unit 51 and an actuating signal 74 to the processor 92 so as to energize the image display unit 82 as well as an actuating signal 75 to the lamp 56 so as to energize the same.

The computer 97 is so designed and constructed to deliver a switching signal 98 depending upon the observation, diagnosis and therapy to be carried out.

A switching unit 99 delivers a command signal 100 or 101 in response to the switching signal 98. In response to the command signal 100, the motor 94 for the optical chopper 93 is energized whereas in response to the command signal 101, shutters 102 and 103 for the optical amplifier 84 and spectroscope 87 are driven.

Mode of operation of the second embodiment will be described.

The therapy of the focuses 55 using the second embodiment is substantially similar to that described above in the first embodiment so that no further description in this connection shall be made in this specification.

In order to diagnose whether the focuses 55 are cancerous, the wavelength tuning element 14 in the titanium-sapphire laser oscillator 9 shown in FIG. 2 is angularly adjusted such that only laser beam with a wavelength of 820 nm is transmitted and laser beams with other wavelengths are absorbed. (In response to the laser beam with the wavelength of 820 nm, the second harmonic generator 17 produces the laser beam with a wavelength of 410 nm in accordance with the relation (1) described above.)

Moreover, HPD which has affinity with cancer tissues and is a photosensitive substance is injected into a blood vessel of a patient. When the focuses 55 are cancerous, HPD is absorbed by cancerous tissues. When irradiated by the laser beam with the wavelength of 410 nm, the HPD-laden focuses 55 are caused to generate fluorescence with a wavelength of 630 nm.

After the injection of HPD, the fiberscope 80 is positioned such that its tip end is substantially in opposing relationship with the focuses 55.

Next, the control panel 95 is manually operated to deliver the command signal 96 for activating the image display unit 82 to the computer 97 as well as the switching signal 98 to the switching unit 99. In response to the signal 98, the switching unit 99 outputs the command signal 101 to open the shutters 103 and 102 of the spectroscope 103 and amplifier 84, respectively.

Furthermore, the control panel 95 is manually operated to deliver the command signal 73 to the YAG laser 52 so as to activate the solid-state laser unit 51.

In response to the command signal 73 applied to the YAG laser 52, the YAG laser oscillator 1 is energized to cause the laser unit 51 to produce laser beam with a wavelength of 532 nm as in the case of the first embodiment described above.

The laser beam with the wavelength of 532 nm enters the laser rod 10 in the titanium-sapphire laser oscillator 9 so that the fundamental wave with a wavelength between 670 and 1100 nm is generated by the rod 10. During resonance of the titanium-sapphire laser fundamental wave by the mirrors 12 and 13, only the titanium-sapphire fundamental wave with a wavelength of 820 nm is transmitted through the wavelength tuning element 14 so that the laser oscillator 9 produces the titanium-sapphire laser fundamental wave with the wavelength of 820 nm.

The fundamental wave thus produced is delivered to the titanium-sapphire second harmonic generator 17 which produces titanium-sapphire laser second harmonic with a wavelength of 410 nm in accordance to the relation (1) described above.

The second harmonic thus produced is delivered to the titanium-sapphire third harmonic generator 18 and the second harmonic having passes through the generator 18 is separated from the laser beams with other wavelengths by the prism 19.

The laser beam with the wavelength of 410 nm separated by the prism 19 is irradiated through the irradiating optical fiber 59 in the fiberscope 80 to the focuses 55.

In this case, the HPD-laden focuses 55 which are cancerous generate fluorescence with a wavelength of 630 nm.

The spectroscope 87 receives fluorescence from the focuses 55 to extract fluorescence with the wavelength of 630 nm which is amplified by the optical amplifier 89 and delivered, as the video signal 88, to the image processor 92.

The image processor 92 converts the video signal 88 to the processed video signal 91 which is applied to the monitor television 65 so that a spectrum of fluorescence from the focuses 55 is graphically displayed.

In order to measure a ratio of the cancerous tissue to the whole focuses 55 by the operation of the control panel 95, the shutter 103 of the spectroscope 87 is closed while the shutter 102 of the optical amplifier 84 is opened so that the solid-state laser unit 51 produces the laser beam with the wavelength of 410 nm which is administered through the fiberscope 80 to irradiate the focuses 55.

When the focuses 55 is cancerous, the HPD-laden focuses 55 generate fluorescence with a wavelength of 630 nm. The optical amplifier 84 receives fluorescence from the focuses 55 and amplifies it to generate the amplified fluorescent signal 83 which is converted to the video signal 85 by the high-sensitive camera 86. The image processor 92 converts the video signal 85 to the processed video signal 91 which is transmitted to the monitor television 65, whereby the fluorescent positions on the focuses 55 are graphically displayed.

Figure 4:
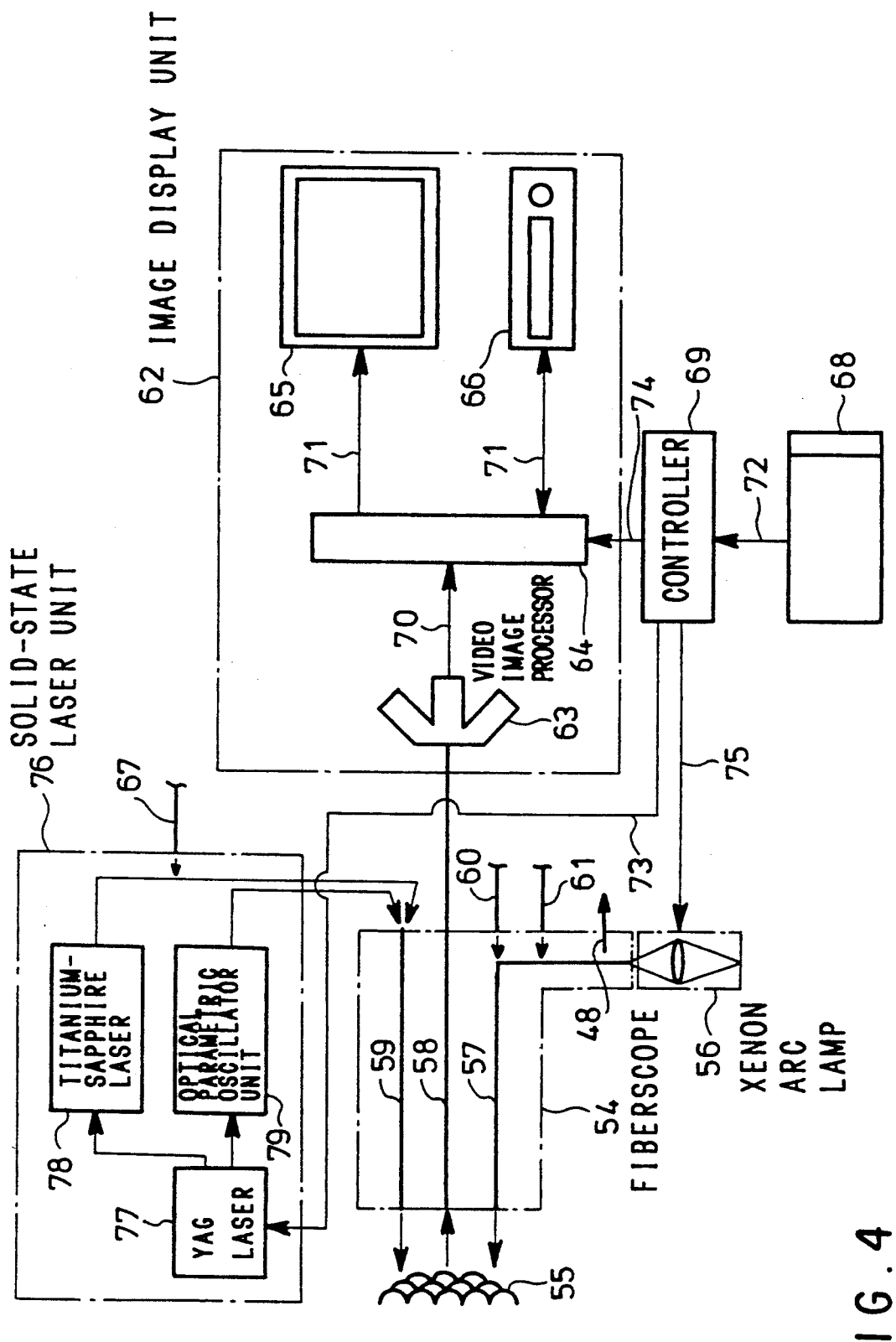
FIG. 4 is a schematic diagram of a third embodiment of the present invention.
Figure 5:
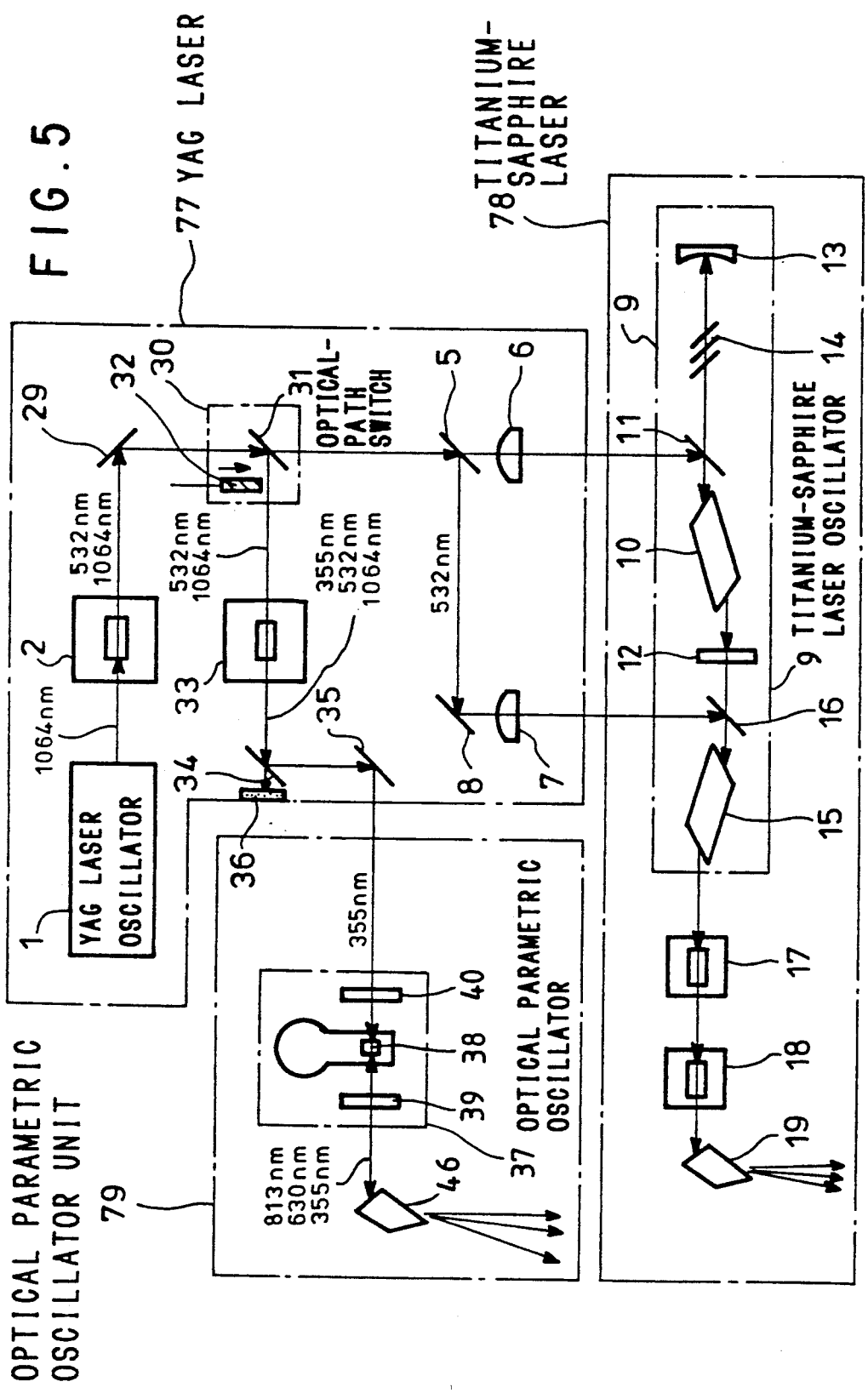
FIG. 5 is a schematic diagram of the solid-state laser unit shown in FIG. 4.

FIGS. 4 and 5 illustrate a third embodiment of the present invention which corresponds to Claim 4 to be claimed hereinafter.

In FIGS. 4 and 5, the fiberscope 54, the xenon arc lamp 56, the image display unit 62, the control panel 68 and the controller 69 are substantially similar in construction to those described in the first embodiment with reference to FIGS. 1 and 2. In FIGS. 4 and 5, parts similar to those shown in FIGS. 1 and 2 are designated by the reference numerals same as shown in FIGS. 1 and 2.

A solid-state laser unit generally designated by numeral 76 comprises a YAG laser 77 for producing the laser beam with a predetermined wavelength, a titanium-sapphire laser 78 which is pumped by the laser beam from the YAG laser 77 to produce laser beam with a predetermined wavelength and a optical parametric oscillator unit 79 which produces laser beam with a predetermined wavelength from the laser beam generated by the YAG laser 77.

Next referring to FIG. 5, the YAG laser 77 in the solid-state laser unit 76 will be described in more detail.

Reference numeral 29 designates a total reflecting mirror for reflecting the YAG laser second harmonic with the wavelength of 532 nm produced by the generator 2 as well as the YAG laser fundamental wave with the wavelength of 1064 nm which has not converted to the second harmonic by the generator 2; and 30, an optical-path switch with its polarizing surface for the YAG laser second harmonic being capable of being angularly displaced through 90 degrees relative to its polarizing surface for the YAG laser fundamental wave, a dichroic polarization mirror 31 and a beam damper 32 for cutting off the beam reflecting from the mirror 31. The YAG laser second harmonic and fundamental wave reflected from the mirror 29 fall on the mirror 31.

When the reflected beam from the mirror 31 is not cut off by the beam damper 32, the switch 30 reflects the YAG laser second harmonic and fundamental wave incident on the mirror 31. On the other hand, when the reflected beam from the mirror 31 is cut off by the beam damper 32, the optical-path switch 30 reflects only the YAG laser fundamental wave incident on the mirror 31 and transmits the YAG laser second harmonic incident on the mirror 31.

Reference numeral 33 denotes a YAG laser third harmonic generator for producing laser beam with a wavelength of 355 nm (YAG laser third harmonic) from the YAG laser second harmonic and fundamental wave reflected from the optical-path switch 30 in accordance with the relation (2) described above; 34, a dichroic mirror which, among the YAG laser fundamental wave and second harmonic having not been converted by the generator 33 and the YAG laser third harmonic produced by the generator 33, passes or transmits only the fundamental wave and the second harmonic and reflects the third harmonic; 35, a total reflecting mirror for reflecting the YAG laser third harmonic reflected from the mirror 34; and 36, a beam damper for cutting off the YAG laser fundamental wave and second harmonic having passed through the mirror 34.

Next still referring to FIG. 5, the titanium-sapphire laser 78 will be described in more detail.

The titanium-sapphire laser 78 is substantially similar in construction to that described above with reference to FIG. 2 except that the titanium-sapphire laser oscillator 24 for generating a difference frequency, the dichroic mirrors 25 and 26, the difference frequency generator 27 and the pellinbroca prism 28 are eliminated and that the laser 78 incorporates a titanium-sapphire laser oscillator 9, a titanium-sapphire laser second harmonic generator 17, a titanium-sapphire third harmonic generator 18 and a pellinbroca prism 19 all of which are substantially similar in construction to those described above in the first embodiment with reference to FIG. 2.

Still referring to FIG. 5, the optical parametric oscillator unit 79 will be described in more detail.

The oscillator unit 79 comprises a optical parametric oscillator 37 which incorporates a non-linear optical crystal 38 such as BBO (betabariumborate) crystal and front and end mirrors 39 and 40 and generates laser beam with a wavelength equal to that of generated beam $\lambda_7$ as well as laser beam with a wavelength equal to that of generated beam $\lambda_8$ from the YAG laser third harmonic reflected from the mirror 35 in accordance with the following relation:

$$\frac{1}{\lambda_9} = \frac{1}{\lambda_7} + \frac{1}{\lambda_8} \quad (4)$$

shere $\lambda_9$: wavelength of pumping beam wave such as YAG laser third harmonic, $\lambda_7$ and $\lambda_8$: wavelengths of generated beam waves; and a pellinbroca prism 46 for separating the laser beams (beams with the wavelengths $\lambda_7$ and $\lambda_8$) generated by the oscillator 37 and the YAG laser third harmonic having not converted by the oscillator 37.

With the non-linear optical crystal 38, the pumping wavelength $\lambda_9$ in Eq. (4) automatically determines wavelengths $\lambda_7$ and $\lambda_8$ of the generated beam waves depending upon the angle of the crystal.

Next, mode of operation will be described.

In the case of therapy of focuses 55, the angle of the non-linear optical crystal 38 shown in FIG. 5 is so determined that one of $\lambda_7$ and $\lambda_8$ in Eq. (4) has a wavelength of 630 nm and the block plate 32 of the optical-path switch 30 is set at inoperative position such that reflection of the laser beam by the mirror 31 is not interrupted.

Under the above described conditions, when the YAG laser fundamental wave with a wavelength of 1064 nm is generated by the YAG laser oscillator 1, the YAG laser second harmonic generator 2 generates YAG laser second harmonic with a wavelength of 532 nm from the YAG laser fundamental wave. The YAG laser second harmonic thus generated and the YAG laser fundamental wave which passes through the YAG laser second harmonic generator 2 are redirected to the YAG laser third harmonic generator 33 by the mirrors 29 and 31 so that the generator 33 generates YAG laser third harmonic with a wavelength of 355 nm in accordance with the relation (2) described above from the YAG laser fundamental wave and second harmonic which pass through the generator 33.

The fundamental wave and second harmonic having passed through the generator 33 pass through the mirror 34 and are cut off by the beam damper 36 while the third harmonic produced by the generator 33 is reflected by the mirrors 34 and 35 to the optical parametric oscillator 37. In response to the third harmonic incident to the oscillator 37, the latter generates laser beams with wavelengths of 630 nm and 813 nm respectively and the third harmonic passes through the oscillator 37. The laser beams with the wavelengths of 630 nm and 813 nm, respectively, generated by the optical parametric oscillator 37 and the YAG laser third harmonic having passed through the oscillator 37 are directed to and separated from each other by the prism 46. The laser beam with the wavelength of 630 nm separated by the prism 46 is administered through the irradiating optical fiber 59 in the fiberscope 54 to irradiate the focuses 55 so that the HPD-laden cancerous tissue is destroyed by the laser beam with the wavelength of 630 nm.

So far the third embodiment has been described with reference to the case where HPD is used. In the case were other photosensitive substance is used, the angle of the non-linear crystal 38 is varied to match a wavelength of the laser beam generated by the optical parametric oscillator 37 with characteristic or absorption band of the photosensitive substance to be used.

Figure 6:
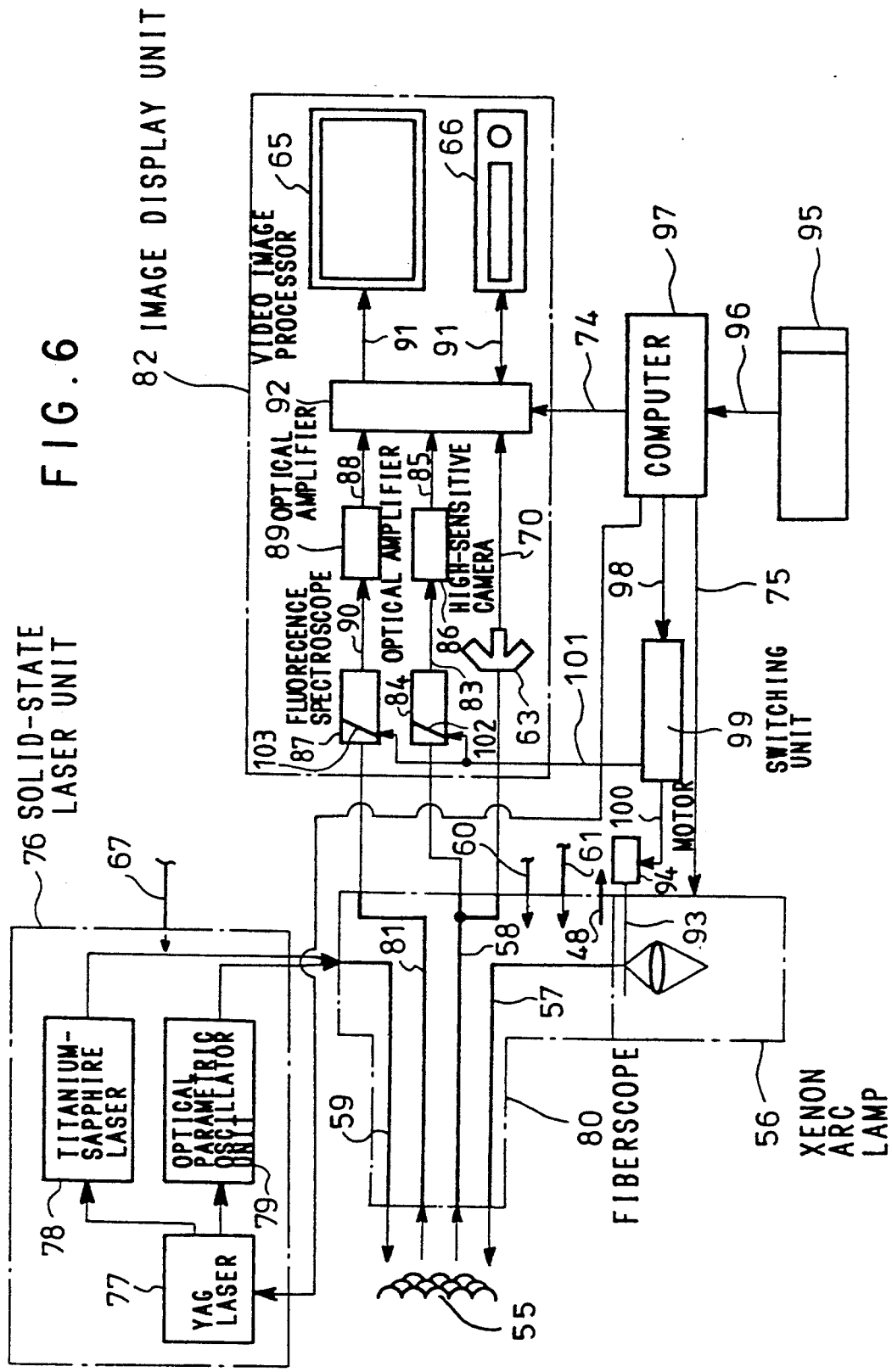
FIG. 6 is a schematic diagram of a fourth embodiment of the present invention.

FIG. 6 illustrates a fourth embodiment of the present invention which is claimed in Claims 5 and 6 hereinafter. The fourth embodiment is substantially similar to the second embodiment shown in FIG. 3 except that the solid-state laser unit 51 is replaced by the solid-state laser unit 76 shown in FIG. 4. The fourth embodiment can also attain the novel features substantially similar to those attained by the second embodiment described above with reference to FIG. 3.

It is to be understood that the present invention is not limited to the embodiments described above and that various modifications may be effected without leaving the true spirit of the present invention. According to the cancer therapy systems of the present invention, the following novel features are attained:

(1) With all of the cancer therapy systems as claimed in Claims 1-6, the laser beam for irradiating focuses is generated by a solid-state laser unit, which eliminates a dye-solution circulator, replacement of dyes and cleaning of the eye-circulator upon replacement of dyes. As a result, maintenance of the cancer therapy system is much facilitated. Use of inflammable dyes and disposal operation of deteriorated dyes are eliminated. Furthermore, a long lifetime of a laser medium or media is ensured.

(2) With the cancer therapy systems as claimed in Claims 1-3, the wavelength of the laser beam to be produced can be varied by changing the angle of the wavelength tuning element so that various types of photosensitive substances can be used.

(3) With the cancer therapy systems as claimed in Claims 4-6, the wavelength of the laser beam to be produced can be varied by changing optical characteristics of the optical parametric oscillator so that various types of photosensitive substances can be also advantageously used.

(4) With the cancer therapy systems as claimed in Claims 2, 3, 5 and 6, in addition to cancer therapy, diagonosis of cancer can be effected.

What is claimed is:

1. A cancer therapy system comprising
    a solid-state laser unit (51) having a YAG laser oscillator (1) for producing YAG laser fundamental wave, a YAG laser second harmonic generator (2) for producing YAG laser second harmonic from the fundamental wave produced by said oscillator (1), a titanium-sapphire laser (9) which is pumped by YAG laser second harmonic generated by said generator (2) to generate titanium-sapphire laser fundamental wave, a titanium-sapphire laser second harmonic generator (17) for generating titanium-sapphire laser second harmonic from said titanium-sapphire laser fundamental wave generated by said laser (9), a difference-frequency-generating YAG laser second harmonic generator (20) which generates YAG laser second harmonic from the YAG laser fundamental wave having not converted to said YAG laser second harmonic by said generator (2), a difference-frequency-generating titanium-sapphire laser oscillator (24) which is pumped by the YAG laser second harmonic generated by said generator (20) to generate titanium-sapphire laser beam fundamental wave and a difference frequency generator (27) which generates difference frequency laser beam from the titanium-sapphire laser fundamental wave generated by said oscillator (24) and the titanium-sapphire laser second harmonic generated by said generator (17),
    a fiberscope (54) for irradiating focuses (55) with the laser beam generated by said laser unit (51) and for observation of said focuses (55), and
    an image display unit (62) for viewing said focuses (55) through said fiberscope (54) and displaying an image of said focuses (55).

2. The system according to claim 1 wherein the image display unit (82) capable of viewing said focuses (55) through the fiberscope (80) serves to graphically display a spectrum of florescence from said focuses (55).

3. The system according to claim 1 wherein the image display unit (82) capable of viewing said focuses (55) through the fiberscope (80) serves to graphically display fluorescent positions on said focuses (55).

4. A cancer therapy system comprising
    a solid-state laser unit (76) having a YAG laser oscillator (1) for producing YAG laser fundamental wave, a YAG laser second harmonic generator (2) for producing YAG laser second harmonic from the fundamental wave produced by said oscillator (1), a titanium-sapphire laser oscillator (9) which is pumped by said YAG laser second harmonic generated by said generator (2) to generate titanium-sapphire laser fundamental wave, a titanium-sapphire laser second harmonic generator (17) for generating titanium-sapphire laser second harmonic from said titanium-sapphire laser fundamental wave generated by said oscillator (9), a YAG laser third harmonic generator (33) for generating the YAG laser third harmonic from the YAG laser fundamental wave having not been converted to the second harmonic by said generator (2) and the YAG second harmonic generated by said generator (2) and an optical parametric oscillator (37) for generating optical parametric oscillating laser beam from the YAG laser third harmonic generated by said generator (33),
    a fiberscope (54) for irradiating focuses (55) with the laser beam generated by said laser unit (76) and observing said focuses (55) and
    an image display unit (62) for photographing said focuses (55) through said fiberscope (54) and displaying an image of said focuses (55).

5. The system according to claim 4 wherein the image display unit (82) capable of viewing said focuses (55) through the fiberscope (80) serves to graphically display a spectrum of florescence from said focuses (55).

6. The system according to claim 4 wherein the image display unit (82) capable of viewing said focuses (55) through the fiberscope (80), serves to graphically displaying fluorescent positions on said focuses (55).

* * * * *